US 011278456B2

(12) United States Patent
Lund

(10) Patent No.: US 11,278,456 B2
(45) Date of Patent: Mar. 22, 2022

(54) TAMPON INSERTION DEVICE

(71) Applicant: Lacey Janell Lund, Springdale, AR (US)

(72) Inventor: Lacey Janell Lund, Springdale, AR (US)

( * ) Notice: Subject to any disclaimer, the term of this patent is extended or adjusted under 35 U.S.C. 154(b) by 0 days.

(21) Appl. No.: 16/934,217

(22) Filed: Jul. 21, 2020

(65) Prior Publication Data

US 2022/0023106 A1   Jan. 27, 2022

(51) Int. Cl.
    *A61F 13/26* (2006.01)

(52) U.S. Cl.
    CPC ............ *A61F 13/266* (2013.01); *A61F 13/26* (2013.01)

(58) Field of Classification Search
    CPC .............................. A61F 13/26; A61F 13/266
    See application file for complete search history.

(56) References Cited

U.S. PATENT DOCUMENTS

| 4,900,299 | A | 2/1990 | Webb |
| 5,206,087 | A | 4/1993 | Tokiwa et al. |
| 5,910,520 | A | 6/1999 | Dabi et al. |
| 6,203,515 | B1 | 3/2001 | Norquest et al. |
| 8,756,791 | B2 | 6/2014 | Jarmon et al. |
| 2010/0100028 | A1 | 4/2010 | Gilbert et al. |
| 2019/0328583 | A1* | 10/2019 | Edgett ................... A61F 13/202 |

OTHER PUBLICATIONS

Mukherjee et al. ("PLA Based Biopolymer Reinforced with Natural Fibre: A Review", J Polym Environ (2011) 19:714-725). (Year: 2011).*

Internet Archive Hemp Filled Polymers—Our Products—Hemp Plastic (Year: 2020).*

Farrugia et al., FDA Send CBD Enforcement Policy to OMB, Issues Cannabis Clinical Research Draft Guidance, and Submits CBD Testing Report to Congress, Jul. 27, 2020, retrieved from https://www.jdsupra.com/legalnews/fda-sends-cbd-enforcement-policy-to-omb-22125/.

Polman, et al., Comparison of the aerobic biodegration of biopolymers and the corresponding bioplastics: a review, Science of the Total Environment 753, available online Aug. 25, 2020, retrieved from https://www.sciencedirect.com/science/article/pii/S0048969720354826.

Titus, et al, Industrial Hemp, Mar./Apr. 2021 Journal of the Kansas Bar Association, retrieved from https://www.ksbar.org/blogpost/1641054/Journal-of-the-Kansas-Bar-Association.

* cited by examiner

*Primary Examiner* — Benjamin J Klein
(74) *Attorney, Agent, or Firm* — Dale J. Ream

(57) ABSTRACT

The tampon insertion device according to the present invention includes a barrel having an insertion end portion and a proximal end portion opposite the insertion end portion and having a continuous side wall extending therebetween that defines an interior area. A tampon is initially positioned in the interior area of the barrel. The tampon insertion device includes a plunger slidably coupled to the barrel that has a first end engaging a proximal end of the tampon, the plunger having a cylindrical configuration selectively slidable from a starter configuration extending away from the proximal end portion of the barrel to a deployed configuration positioned downstream inside the interior area of the barrel. Pressure applied to the plunger causes the plunger to urge the tampon downstream within the interior area of the barrel. The tampon insertion device, i.e. the tampon applicator, is constructed using a material consisting essentially of hemp plastic.

15 Claims, 4 Drawing Sheets

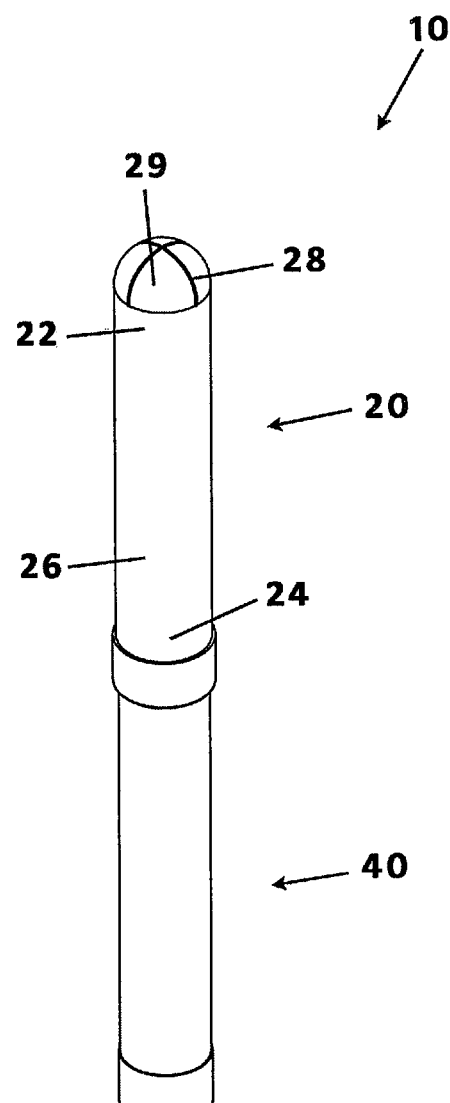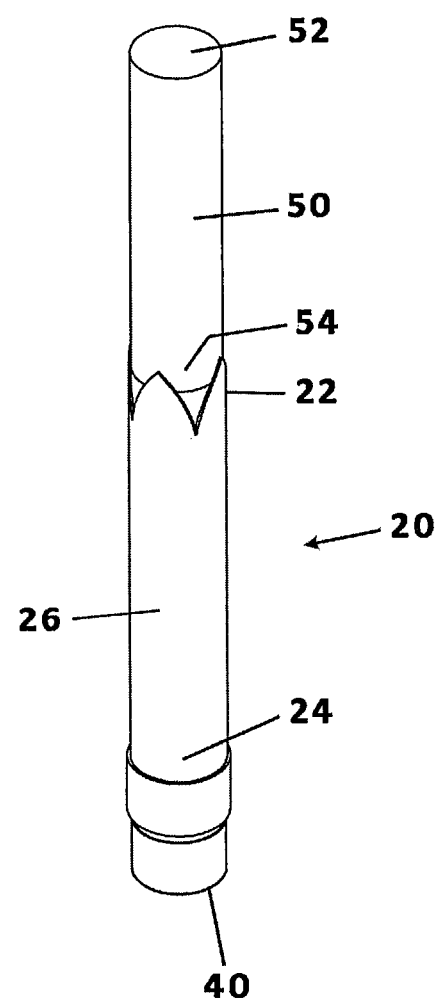
Fig.1a
Fig.1b

TAMPON INSERTION DEVICE

FIELD OF THE INVENTION

This invention relates generally to tampon delivery devices and, more particularly, to a tampon insertion device having a barrel constructed using a process that includes hemp plastic.

SUMMARY OF THE INVENTION

The tampon insertion device according to the present invention includes a barrel having an insertion end portion and a proximal end portion opposite the insertion end portion and having a continuous side wall extending therebetween that defines an interior area. A tampon is initially positioned in the interior area of the barrel. The tampon insertion device includes a plunger slidably coupled to the barrel that has a first end engaging a proximal end of the tampon, the plunger having a cylindrical configuration selectively slidable from a starter configuration extending away from the proximal end portion of the barrel to a deployed configuration positioned downstream inside the interior area of the barrel. Pressure applied to the plunger causes the plunger to urge the tampon downstream within the interior area of the barrel.

The tampon insertion device, i.e. the tampon applicator, is constructed using a material consisting at least partially of hemp plastic so as to apply the benefits therefrom to a woman's health and the environment, and to provide a rigid yet flexible construction. Currently, hemp plastic has not been applied or proposed to feminine-care products such as tampons. Hemp plastic is considered as a leading material of the future and has been applied in the past to automobile construction for its strength and anti-denting properties. To date, however, a tampon applicator has not been constructed using hemp materials in that strength and anti-denting properties are not desirable or possible. However, the inventor has identified reasons that make it desirable to construct the tampon insertion device using hemp plastic. Namely, a barrel and plunger constructed of hemp plastic would be biodegradable. This is important for at least two reasons, including (1) reducing a woman's contact with petrochemical-based plastic is safer, and (2) the tampon insertion device would be biodegradable and not add to the overburden of landfills currently full of traditional plastic products.

Hemp plastic is a bioplastic made using industrial hemp. There are many different types of hemp plastic—from standard plastics reinforced with hemp fibers, to a 100% hemp plastic made entirely from the hemp plant. Hemp plastic is recyclable and can be manufactured to be 100% biodegradable.

With even more particular reference to hemp plastic use, hemp plastic is superior over traditional petroleum-based plastic historically used in tampon applicators. Specifically, hemp plastic is stronger than petroleum-based products. In fact, plastic made from hemp is five times stiffer and 3.5 times stronger than polypropylene which is one of the most common types of traditional plastic. Hemp plastic is also much lighter than traditional plastic. Being exponentially lighter and stronger make hemp plastic desirable and unique as applied to the present invention. And this makes hemp plastic not only superior—but safer.

Therefore, a general object of this invention is to provide a tampon insertion device having a barrel and plunger that are constructed at least partially of hemp plastic.

Another object of this invention is to provide a tampon insertion device, as aforesaid, that is hygienic and safe to the health of women using the device.

Still another object of this invention is to provide a tampon insertion device, as aforesaid, that is biodegradable.

Yet another object of this invention is to provide a tampon insertion device, as aforesaid, that is stiffer, lighter, and stronger than a tampon insertion device constructed of oil-based plastic yet maintains the necessary flexibility.

Other objects and advantages of the present invention will become apparent from the following description taken in connection with the accompanying drawings, wherein is set forth by way of illustration and example, embodiments of this invention.

BRIEF DESCRIPTION OF THE DRAWINGS

FIG. 1a is a perspective view of a tampon insertion device according to a preferred embodiment of the present invention, illustrated in ready to use or retracted configuration;

FIG. 1b is another perspective view of the tampon insertion device as in FIG. 1a, illustrated in a deployed or extended configuration;

FIG. 3a is a top view of the tampon insertion device as in FIG. 1a;

FIG. 3b is a sectional view taken along line 3b-3b of FIG. 3a;

FIG. 4b is a sectional view taken along line 4b-4b of FIG. 4a.

DESCRIPTION OF THE PREFERRED EMBODIMENT

Figure 2:
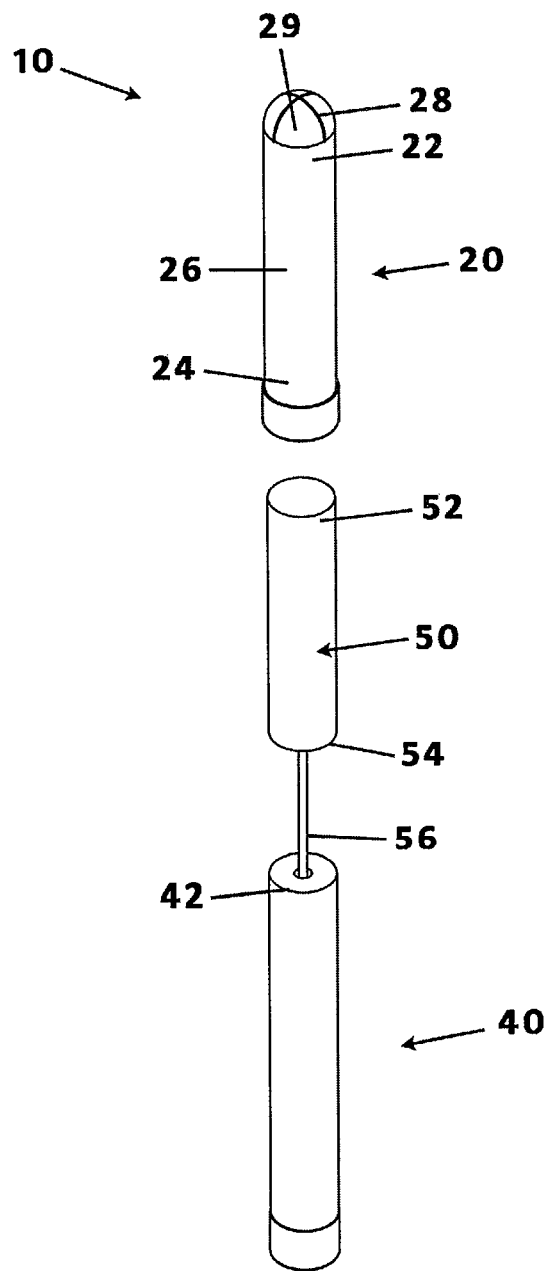
FIG. 2 is an exploded view of the tampon insertion device as in FIG. 1
Figure 3A:
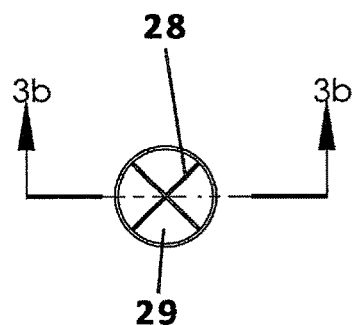
Figure 3B:
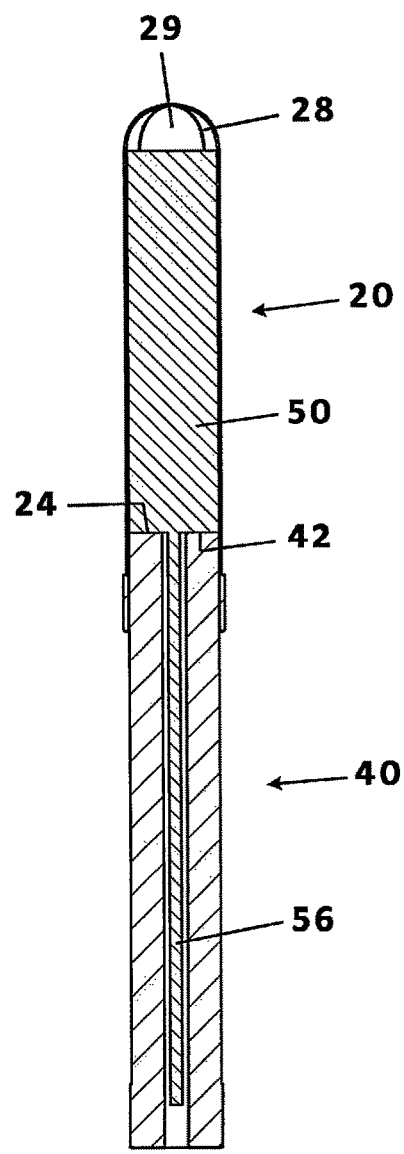

A tampon insertion device according to a preferred embodiment of the present invention will now be described in detail with reference to FIGS. 1a to 4b of the accompanying drawings. The tampon insertion device 10, also referred to as a tampon applicator, includes a barrel 20, a tampon 50 initially positioned in the barrel 20, a plunger 40 for pushing the tampon 50 out of the barrel. Specific reference will be made to a process of making the barrel 20 and plunger 40 using a process that includes hemp plastic.

The barrel 20 has an insertion end portion 22 and a proximal end portion 24 opposite the insertion end portion 22, i.e. opposed ends. While the proximal end portion 24 defines an open end, the insertion end portion 22 is initially closed but then opens up as a tampon 50 is pushed out as will be described later. More particularly, a continuous side wall 26 extends between the proximal end portion 24 and the insertion end portion 22, the continuous side wall 26 having a cylindrical configuration that defines an interior area into which other components are situated and some of which move slidably as will be described.

The insertion end portion 22 includes a two or more (also referred to as a plurality) of lines of separation 28 that divides the insertion portion into a plurality of flaps 30 or panels. Initially, the plurality of flaps may have a curved end or domed configuration that limit access to the interior area (FIG. 1a) but that separate to form or define an open end when the tampon 50 is pushed downstream and out of the interior area of the barrel 20 (FIG. 1b), as will be described in more detail below.

Further, the tampon 50 is initially positioned within the interior area of the barrel 20 and is configured to move slidably when pushed or urged downstream by operation of the plunger 40 as explained below. The tampon 50 may be constructed of cotton or a blend of materials suitable to absorb blood and other fluids common to a woman's menstrual period. More particularly, the tampon 50 may have a cylindrical configuration with a flat or truncated distal end 52 (i.e. the upper end). Further, the tampon 50 may include a proximal end 54 opposite the distal end 52 from which a string 56 extends. The string enables a user to extract the tampon 50 more efficiently. In one embodiment, a wax plug (not shown) may be included on the string 56 to absorb blood and to enhance grip.

Figure 4A:
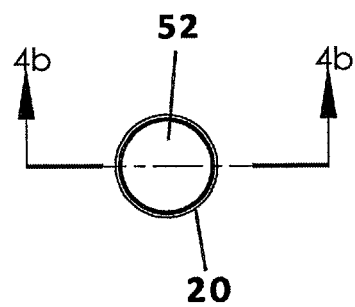
FIG. 4a; is a top view of the tampon insertion device in a partially deployed configuration.
Figure 4B:
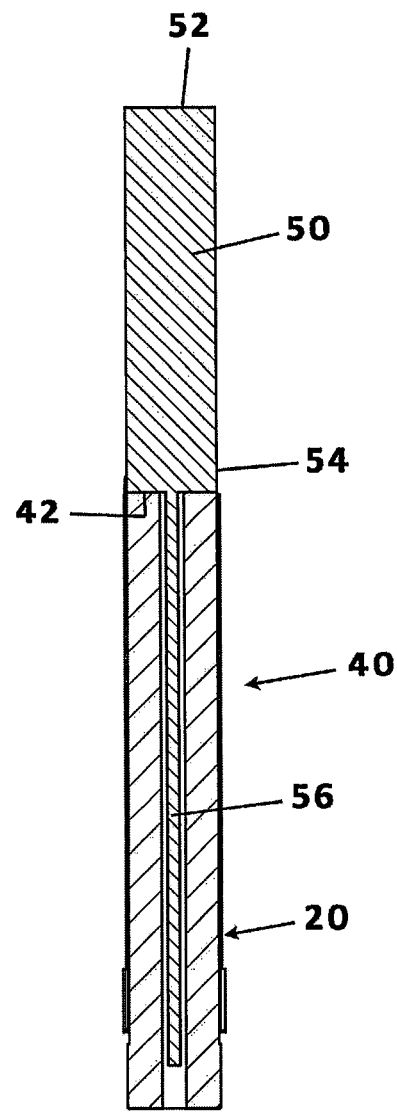

The tampon insertion device 10 includes a plunger 40 configured to move slidably in the barrel 20. More particularly, the plunger 40 may have a tubular or cylindrical configuration that enters the barrel 20 via the proximal end portion 24 and has a first end 42 (i.e. the upper end as illustrated) that engages and bears against a lower end of the tampon 50. The plunger 40 is configured to move downstream toward the insertion end portion 22 when pressure is applied thereto by the hand of a user, downstream movement of the tampon 50. In an embodiment, the plunger 40 may be pushed downstream in the barrel 20 and moves slidably. Continued pressure on the plunger 40 causes the tampon to be pushed out of the insertion end portion 22 (FIG. 4). In some embodiments, the plunger 40 may be threadably linked to the barrel 20 such that a twisting of the plunger 40 results in movement between a starter configuration extending outwardly away from the barrel 20 and a deployed configuration substantially or completely inside the interior area of the barrel 20.

As is described in greater detail herein, in various embodiments of the invention, the tampon applicator may be made exclusively, or at least partially of, hemp plastic. No material other than hemp plastic may be necessary or preferred; however, in some embodiments, the addition of biodegradable polymer(s) may be added to the hemp plastic for construction of the barrel and plunger. Hemp plastic refers to hemp plant fibers that may be extracted and combined with polymers in a manufacturing process. More particularly, Hemp, or industrial hemp, is a strain of the *Cannabis sativa* plant species that is grown specifically for the industrial uses of its derived products. A *cannabis* fibrous tampon applicator is novel and non-obvious.

Hemp plastic can be entirely biodegradable when made or combined with biodegradable polymers. A biodegradable polymer is a polymer that can be decomposed by bacteria. Examples of biodegradable polymers which can broken down by micro-organisms within a suitable amount of time include polyglycolic acid (PGA), polyhydroxy butyrate (PHB), polyhydroxy butyrates-co-beta hydroxyl valerate (PHBV), polycaprolactone (pcl), nylon-2-nylon-6. If made properly and in the right environment, hemp plastic can decompose in 3 to 6 months which is unexpected in view of petroleum-based plastic which are toxic and degrade very little even after decades.

Now with further reference to the tampon applicator and, specifically, to the barrel 20 and plunger 40, in embodiments, the barrel 20 and plunger 40 consist essentially of hemp plastic rather than petrochemical plastics. In the embodiments, the basic and novel characteristic of the invention is that the barrel 20 and the plunger 40 are constructed of hemp plastic such that the applicator is entirely biodegradable and is at least two times stronger than conventional applicators while maintaining the flexibility necessary to operate the applicator according to standard operation.

In some embodiments, the material forming the tampon applicator, and more specifically the barrel 20 and the plunger 40, consists essentially of a combination of a hemp plastic and a biodegradable polymer or polymers. Here, the basic and novel characteristics of the invention are that the applicator is formed essentially of a combination of hemp plastic and a biodegradable polymer such that the applicator is biodegradable and maintains a strength of at least two times the strength of conventional plastics.

More particularly, hemp plants may be harvested, broken down into essential components for production of the barrel 20 and plunger 40 of the tampon insertion device 10. The tampon 50 may be inserted into the barrel 20 prior to packaging. Constructed of hemp plastic, the barrel and, in an embodiment where both the barrel and plunger are constructed of hemp plastic, the overall tampon applicator exhibits a firmness and certain lack of flexibility that is both unexpected and highly desirable, while maintaining the necessary flexibility such that operation of the applicator may proceed according to conventional wisdom. Specifically, a tampon applicator constructed of hemp-plastic overcomes a problem typical with tampons constructed of traditional or petroleum-based plastic—namely to bend and become difficult to locate when lodged in a woman's vagina. The advantages of hemp plastic are only experienced when the tampon applicator recited in the present claims is constructed essentially of hemp plastic, or a combination of hemp plastic and biodegradable polymer(s).

According to further embodiments, the tampon applicator may be constructed only of hemp plastic, with only slight amounts of naturally occurring impurities or impurities that are introduced by virtue of the processing process. In such embodiments, the applicator may exhibit strength properties that are superior to conventional applicators.

In still other embodiments, the tampon applicator is constructed only of hemp plastic together with a biodegradable polymer, such as the biodegradable polymers described herein. In such embodiments, the applicator may further include slight amounts of naturally occurring impurities, or impurities that are introduced into the material during the manufacturing process. According to some aspects, the applicator is constructed of about 1-100 wt % hemp plastic and about 0-99 wt % biodegradable polymer or polymers. In further aspects, the applicator is constructed of about 10-100 wt %, about 20-100 wt %, about 30-100 wt %, or about 40-100 wt % hemp plastic, and the remainder biodegradable polymer or polymers. According to still further aspects, the applicator consists of at least about 50 wt % hemp plastic and the remainder biodegradable polymer or polymers. In some embodiments it may be preferable for the amount of hemp plastic to be greater than about 50 wt %, greater than about 60 wt %, greater than about 70 wt %, greater than about 80 wt %, or greater than about 90 wt %, with the remainder, if any, being biodegradable polymer or polymers. In use, a user inserts the barrel 20 of the tampon insertion device 10 into her vagina. Specifically, then, the user may push or rotate the plunger 40 upwardly into the barrel 20 so as to urge the tampon 50 upwardly, i.e. downstream. The tampon 50 is, thus, deployed into the vagina.

It is understood that while certain forms of this invention have been illustrated and described, it is not limited thereto except insofar as such limitations are included in the following claims and allowable functional equivalents thereof.

The invention claimed is:

1. A tampon insertion device for insertion of a tampon, comprising:
   a barrel having an insertion end portion and a proximal end portion opposite said insertion end portion and having a continuous side wall extending therebetween that defines an interior area; and
   a tampon initially positioned in said interior area of said barrel;
   wherein said barrel consists of a hemp-fiber reinforced biopolymer.

2. The tampon insertion device as in claim 1, wherein said barrel is biodegradable.

3. The tampon insertion device as in claim 2, wherein said insertion end portion includes multiple lines of separation configured to separate and define an open end when said plunger is moved toward said deployed configuration.

4. The tampon insertion device as in claim 1, further comprising:
   a plunger operably coupled to said barrel and having a first end engaging a proximal end of said tampon, said plunger having a cylindrical configuration selectively slidable from a starter configuration extending away from the proximal end portion of the barrel to a deployed configuration positioned inside the barrel;
   wherein pressure applied to said plunger causes said plunger to urge said tampon downstream within said interior area of said barrel.

5. The tampon insertion device as in claim 4, wherein said plunger consists of a hemp-fiber reinforced biopolymer.

6. The tampon insertion device as in claim 5, wherein said biopolymer of said plunger is the same as said biopolymer of said barrel.

7. A tampon insertion device for insertion of a tampon, comprising:
   a barrel having an insertion end portion and a proximal end portion opposite said insertion end portion and having a continuous side wall extending therebetween that defines an interior area;
   a tampon initially positioned in said interior area of said barrel; and
   a plunger operably coupled to said barrel and having a first end engaging a proximal end of said tampon, said plunger having a cylindrical configuration selectively slidable from a starter configuration extending away from the proximal end portion of the barrel to a deployed configuration positioned inside the barrel;
   wherein said barrel and said plunger are comprised of about 1-100 wt % of a hemp-fiber reinforced biopolymer;
   wherein pressure applied to said plunger causes said plunger to urge said tampon downstream within said interior area of said barrel.

8. The tampon insertion device as in claim 7, wherein said barrel is biodegradable.

9. The tampon insertion device as in claim 8, wherein said barrel comprises about 1-99 wt % of said biopolymer and about 1-99 wt % of said hemp fibers.

10. The tampon insertion device as in claim 7, wherein said plunger is completely biodegradable.

11. The tampon insertion device as in claim 10, wherein said plunger comprises about 1-99 wt % of said biopolymer and about 1-99 wt % of said hemp fibers.

12. The tampon insertion device as in claim 7, wherein said insertion end portion includes multiple lines of separation configured to separate and define an open end when said plunger is moved toward said deployed configuration.

13. A tampon insertion device for insertion of a tampon, comprising:
   a barrel constructed of hemp plastic material comprising at least one biodegradable polymer and a plurality of hemp fibers, said barrel having an insertion end portion and a proximal end portion opposite said insertion end portion and having a continuous side wall extending therebetween that defines an interior area;
   a tampon initially positioned in said interior area of said barrel;
   a plunger consisting of hemp plastic material comprising at least one biodegradable polymer and a plurality of hemp fibers, said plunger being operably coupled to said barrel and having a first end engaging a proximal end of said tampon, said plunger having a cylindrical configuration selectively slidable from a starter configuration extending away from the proximal end portion of the barrel to a deployed configuration positioned inside the barrel;
   wherein pressure applied to said plunger causes said plunger to urge said tampon downstream within said interior area of said barrel.

14. The tampon insertion device as in claim 13, wherein said at least one biodegradable polymer of said barrel is the same as said at least one biodegradable polymer of said plunger.

15. The tampon insertion device as in claim 13, wherein said insertion end portion includes multiple lines of separation configured to separate and define an open end when said plunger is moved toward said deployed configuration.

* * * * *